United States Patent [19]
Sun et al.

[11] Patent Number: 5,795,304
[45] Date of Patent: Aug. 18, 1998

[54] SYSTEM AND METHOD FOR ANALYZING ELECTROGASTROPHIC SIGNAL

[75] Inventors: Hun H. Sun, Blue Bell; Wen Wei Qiao, Drexel Hill, both of Pa.; William Y. Chey, Pittsford; Kae Yol Lee, Rochester, both of N.Y.

[73] Assignee: Drexel University, Philadelphia, Pa.

[21] Appl. No.: 827,086

[22] Filed: Mar. 26, 1997

Related U.S. Application Data

[60] Provisional application No. 60/014,892, Mar. 27, 1996.
[51] Int. Cl.[6] ................................................ A61B 5/0488
[52] U.S. Cl. ................................................ 600/546
[58] Field of Search ............................... 600/513, 546, 600/300, 301, 547, 593

[56] References Cited

U.S. PATENT DOCUMENTS 5,560,370  10/1996  Verrier et al. ............... 600/518
5,601,088   2/1997  Swanson et al. ............. 600/546

*Primary Examiner*—Scott M. Getzow
*Attorney, Agent, or Firm*—Panitch Schwarze Jacobs & Nadel, P.C.

[57] ABSTRACT

A method and system for analyzing an electrogastrophic (EGG) signal are disclosed. Electrodes are positioned on abdominal skin of a subject adjacent a stomach thereof. The electrodes obtain the EGG signal produced by the stomach. An amplifier is connected to the electrodes, receives the obtained EGG signals, and amplifies the obtained EGG signal. A transforming device is operatively connected to the amplifier. The transforming device receives the amplified EGG signal and transforms the amplified EGG signal from a time domain representation to a frequency domain representation. The transformation is accomplished by way of a predetermined transform function incorporating a variable frequency and a window function. The window function has a time resolution and a frequency resolution. The frequency resolution of the window function is proportional to the frequency. The time resolution of the window function varies with the frequency such that the time resolution is relatively narrow when the frequency is relatively high and relatively broad when the frequency is relatively low.

14 Claims, 17 Drawing Sheets

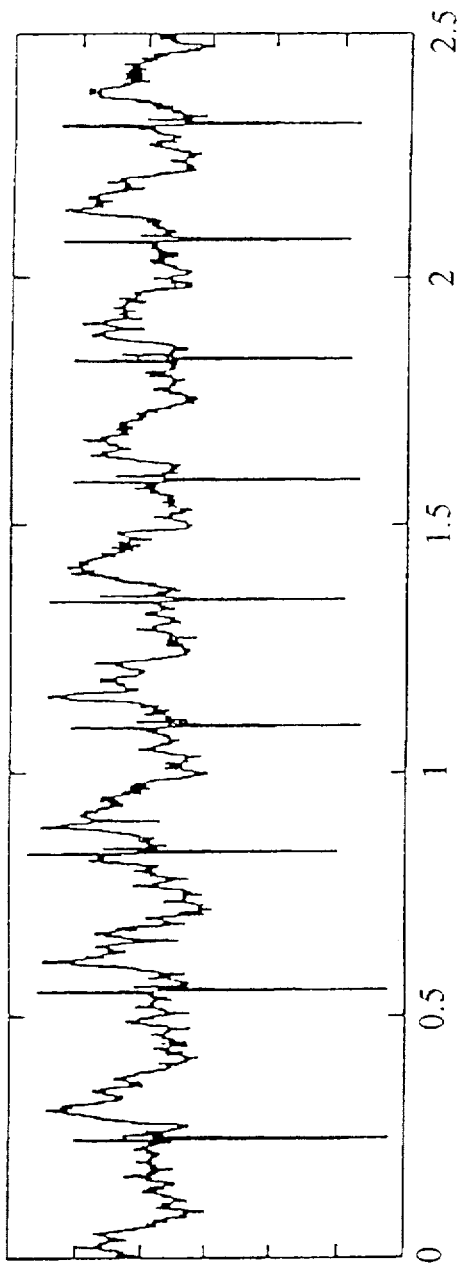
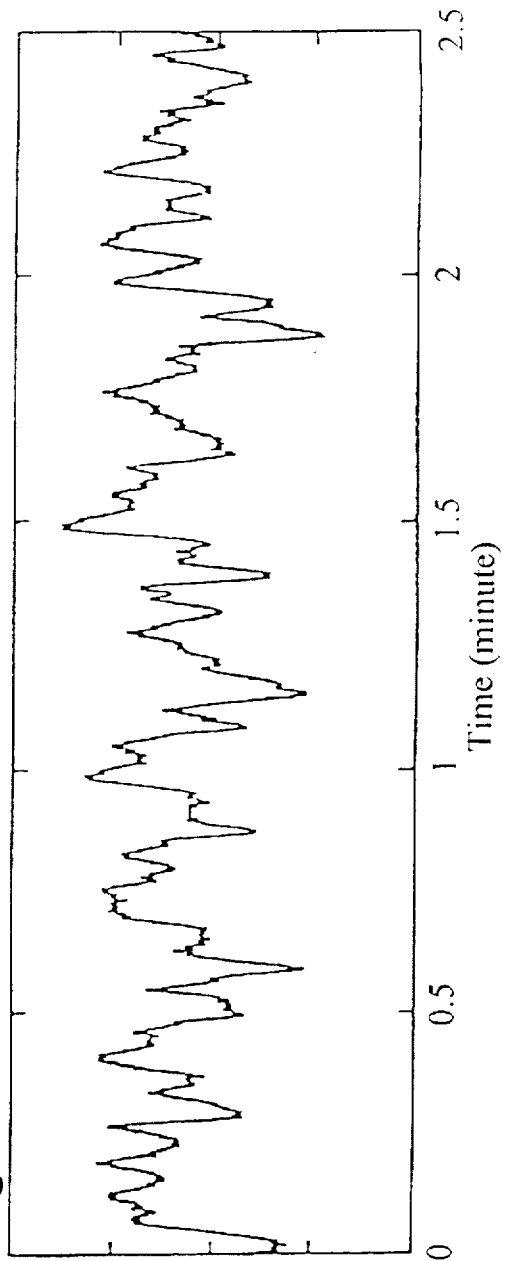

SYSTEM AND METHOD FOR ANALYZING ELECTROGASTROPHIC SIGNAL

BACKGROUND OF THE INVENTION

This application claim benefit under USC 119(c) of any U.S. Provisional application No. 60/014,892, filed Mar. 27, 1996.

The present invention generally relates to a system and method for analyzing a non-stationary electrical body signal by way of a continuous wavelet transform. In particular, the present invention relates to a system and method for analyzing an electrogastrophic signal from a stomach of a subject.

As is known, in electrogastrophy, the electrogastrophic (EGG) signal associated with a stomach may be examined to detect 'slow waves' and occurrences of a high frequency component (i.e., 'spike activity'). Such detected slow waves and spike activity have important clinical and diagnostic significance. The characteristics of slow waves and spike activity are normally observed and identified from recordings made at the serosal surface of the stomach. However, this usually requires that mucosal suction electrodes be orally or rectally inserted or surgically implanted on the serosal surface. As should be evident, such invasive techniques are expensive, relatively difficult, uncomfortable to the patient, and can result in the introduction of infecting agents. Accordingly, a non-invasive method to detect the slow waves and the spike activity from an abdominal surface recording is preferred.

Present abdominal recording techniques, however, suffer from several severe problems. Most importantly, the EGG signal is by its nature a non-stationary signal in terms of its frequency, amplitude and wave shape. These 'abnormalities' carry relevant information for diagnostic purpose. Traditional filtering techniques are not feasible solutions, however, because such traditional techniques require a stationary signal. A need exists, then, for a system and method for processing an abdominal EGG signal that is capable of handling a non-stationary signal, which is much more difficult and complicate to implement than the stationary case.

BRIEF SUMMARY OF THE INVENTION

The aforementioned need is satisfied by a method and system for analyzing an electrogastrophic (EGG) signal. Electrodes are positioned on abdominal skin of a subject adjacent a stomach thereof. The electrodes obtain the EGG signal produced by the stomach. An amplifier is connected to the electrodes, receives the obtained EGG signals, and amplifies the obtained EGG signal. A transforming device is operatively connected to the amplifier. The transforming device receives the amplified EGG signal and transforms the amplified EGG signal from a time domain representation to a frequency domain representation. The transformation is accomplished by way of a predetermined transform function incorporating a variable frequency and a window function. The window function has a time resolution and a frequency resolution. The frequency resolution of the window function is proportional to the frequency. The time resolution of the window function varies with the frequency such that the time resolution is relatively narrow when the frequency is relatively high and relatively broad when the frequency is relatively low.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIGS. 2A and 2B are timing diagrams showing, respectively, serosal and abdominal EGG signals with spike activity;

DETAILED DESCRIPTION OF THE INVENTION

Stomach Activity

In the stomach, electrical slow waves (also called pacesetter potentials) originate in the putative pacemaker region near the junction of the proximal one third and the distal two third of the gastric body along the greater curvature. Slow waves normally appear every 10–30 seconds (2–6 cycles per minute (cpm), and propagate along the stomach body down to the corpus and antrum with increases of amplitude and velocity. However, the frequency remains the same along the path of the propagation. Gastric electrical dysrhythmia are often reflected in the frequency abnormality of the slow wave. Tachygastria is associated with nausea, vomiting, abdominal pain, and motion sickness, and the slow wave frequency associated therewith is about 5–9 cpm. The slow wave frequency associated with bradygastria, which is found in association with strong antral contractions, is about less than 2 cpm. Arrhythmia is reflected by irregular or absent rhythmic activity.

Studies show that gastric dysrhythmia is usually of brief duration. For example, in observed short bursts of both tachygastria and bradygastria, it has been found that the median duration of these dysrhythmic episodes ranges from 2 to 10 minutes. Slow wave variances in amplitude and frequency can also be normal for a healthy subject. For example, the response of the EGG signal to a meal is usually an increase of slow wave amplitude and frequency. In fact, the amplitude can be almost doubled.

Figure 1A:
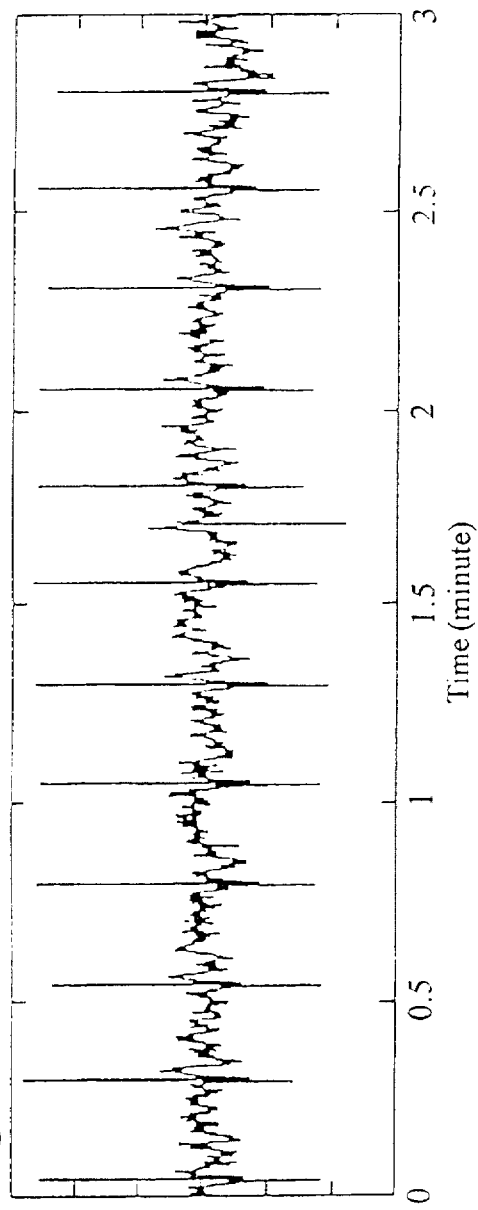
FIGS. 1A and 1B are timing diagrams showing, respectively, serosal and abdominal EGG signals without spike activity.
Figure 1B:
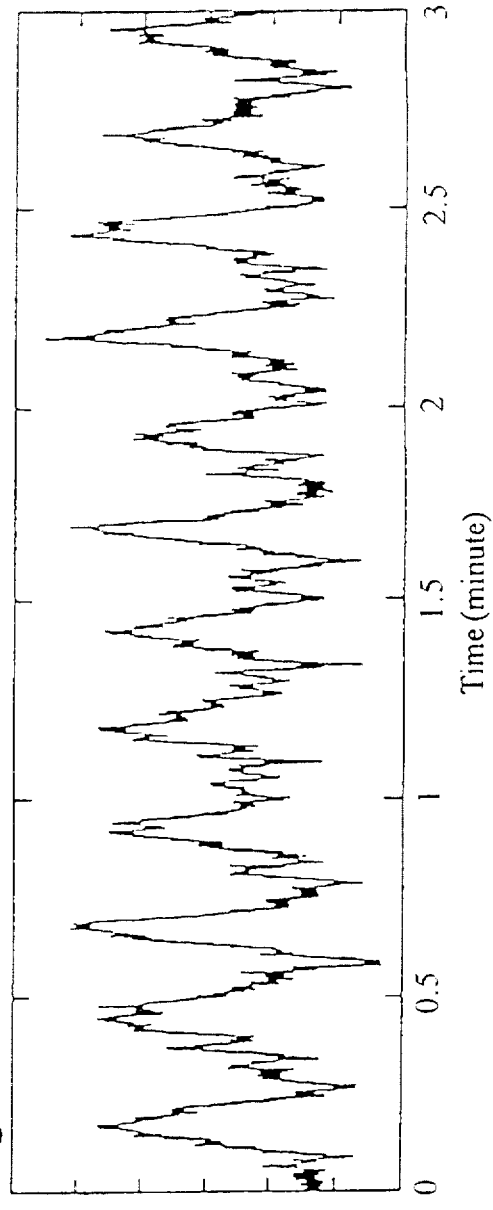

As seen in FIG. 1A, the slow waves of a serosal EGG signal are triphasic, with a large positive potential preceded and followed by smaller deflections. When the stomach contracts, this triphasic event may be followed by a second electrical transient which is called an action potential or a spike, as shown in FIG. 2A. It is this action potential that causes the mechanical contraction of the stomach, mixes food with gastric juice, subdivides the food, and urges the food toward the duodenum and small intestines. FIGS. 1B and 2B show abdominal EGG signals corresponding to the serosal EGG signals of FIGS. 1A and 2A, respectively. As seen, the abdominal EGG signal with the high frequency component (i.e., 'the spike activity') (FIG. 2B) usually consists of small ripples in each slow wave cycle with a frequency about 4 to 5 times of that of the slow waves. Although the source of the high frequency component has as yet not been determined, such component is still believed to be significant.

Time Frequency Analysis

As mentioned above, the electrogastrophic (EGG) signal is a non-stationary signal. Accordingly, its properties such as frequency, amplitude, phase, etc. in the slow waves, as well as in the appearance of the spike activity, change with time, subject, and subject's health condition. It is therefore not suitable for conventional Fourier transform analysis. Let us first consider a signal x(t) and its Fourier transform as:

$$X^{FT}(f) = \int_{-\infty}^{\infty} x(t) e^{-j2\pi ft} dt \quad (1)$$

which is computed as the inner product of the signal with sinusoidal wave as basis function of infinite duration extending from the beginning to the end of the segment of the signal. In the computation, it is assumed that the frequencies of the sinusoidal waves do not change with time so that the signal properties will be the same from the beginning to the end. That is, it is assumed that the signal is stationary. If the signal x(t) is non-stationary, then any abrupt change of the signal in the time domain will be spread out over the entire frequency domain because the frequency domain is derived by integrating the time domain from the beginning to the end. Accordingly, it can not be ascertained when the change occurred. Therefore, an analysis adapted to non-stationary signals requires more than the Fourier transform.

Short-time Fourier Transform (STFT)

One usual approach to analyzing a non-stationary signal is to introduce time dependency in the Fourier analysis while preserving linearity. Accordingly, a 'local frequency' parameter (local in time) is introduced so that the 'local' Fourier transform looks at the signal through a window over which the signal is approximately stationary. This is called short-time Fourier transform (STFT), or windowed Fourier transform as well as running spectrum analysis.

The STFT of a signal x(t) is defined as:

$$X^{STFT}(f, \tau) = \int_{-\infty}^{\infty} x(t) e^{-j2\pi ft} w(t - \tau) dt \quad (2)$$

where w(t–τ) is a window located at time τ. From Eq. (2), the one-dimensional signal x(t), a function of time, is converted into a two-dimensional function of the time variable τ and the frequency variable f.

Eq. (2) can be interpreted as the Fourier transform of x(t) viewed through the window w(t–τ). The window has a stationary origin and as τ changes, the signal slides past the window so that at each value of τ, a different portion of the signal is viewed. Many types of windows have been discussed and one window for STFT is the Gaussian function:

$$w(t) = g_\alpha(t) = \frac{1}{2\sqrt{\pi\alpha}} e^{\frac{t^2}{4\alpha}} \quad (3)$$

where α is the standard deviation and α>0 is fixed. Sometimes, the Gaussian function of Eq. (3) is also called the 'optimal' window for STFT and the optimality is characterized by the uncertainty principle discussed below.

The primary purpose of the STFT is to limit the extent of the signal to be transformed so that the spectral characteristics are reasonably stationary over the duration of the window. The width of the window is determined by the (fixed) positive constant α. To select a measurement of the width of the window function, the notion of standard deviation, or root mean square (RMS) duration, is employed, as defined by:

$$\Delta t^2 = \frac{\int t^2 |g_\alpha(t)|^2 dt}{\int |g_\alpha(t)|^2 dt} = \alpha \quad (4)$$

Note that since $g_\alpha(t)$ is an even function, its center is 0, and hence the time width of the window function is:

$$2\Delta t = 2\sqrt{\alpha} \quad (5)$$

An alternative view of the STFT is based on interpretation of the filtering process. At a given frequency f, Eq. (2) is the inner production of the signal x(t) and a bandpass filter $e^{j2\pi ft}g_\alpha(t)=g_b(t)$: where $g_b{}^*(t)$ represents the conjugate of $g_b(t)$. In other words, instead of considering $$X^{STFT}(f, \tau) = \int_{-\infty}^{\infty} x(t) g_b{}^*(t - \tau) dt = \int_{-\infty}^{\infty} x(t) g_\alpha(t - \tau) e^{-j2\pi ft} dt \quad (6)$$

the STFT as time-localization of the Fourier transform of x(t), it may be interpreted as filtering the signal x(t) by using a bandpass filter function $g_b(t)=e^{j2\pi f_o t} g_\alpha(t)$:

$$g_b(t) = \frac{1}{2\sqrt{\pi\alpha}} e^{\frac{t^2}{4\alpha}} e^{j2\pi f_o t} \quad (7)$$

where $f_o$ is the center frequency of the filter bank. The bandwidth of the window function in the frequency domain can be determined by:

$$\Delta f^2 = \frac{\int f^2 |G_\alpha(f)|^2 df}{\int |G_\alpha(f)|^2 df} = \frac{1}{(4\pi)^2 \alpha} \quad (8)$$

where $G_\alpha(f)$ is the Fourier transform of the Gaussian function $g_\alpha(t)$:

$$G_\alpha(f) = \int_{-\infty}^{\infty} g_\alpha(t) e^{-j2\pi ft} dt \quad (9)$$

Also, since $G_\alpha(f)$ is an event function, its center is 0, and hence the bandwidth of the window function is:

$$2\Delta f = \frac{1}{2\pi\sqrt{\alpha}} \quad (10)$$

As can be seen, the STFT investigates an analog signal x(t) at t=τ by using the window function $g_\alpha(t-\tau)$ as defined in Eq. (3), or by observing the spectrum of x(t) in a neighborhood of the frequency f by using the window function $G_\alpha(f)$ as defined in Eq. (9). The product of the width of the time-window $g_\alpha$ and that of the frequency-window $G_\alpha$ is:

$$(2\Delta t) \cdot (2\Delta f) = \frac{1}{\pi} \quad (11)$$

The Cartesian product $$|\tau - \sqrt{\alpha}, \tau + \sqrt{\alpha}| \times \left[ f - \frac{1}{4\pi\sqrt{\alpha}}, f + \frac{1}{4\pi\sqrt{\alpha}} \right] \quad (12)$$

of the two windows is called a rectangular time-frequency window. A plot of this window is shown in FIG. 3.

Figure 3:
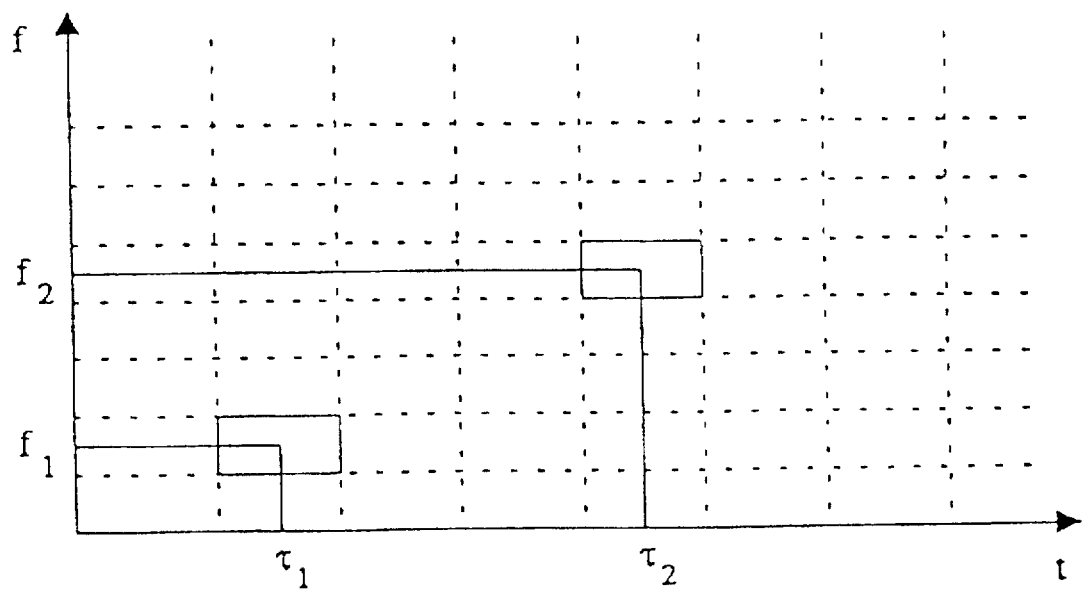
FIG. 3 is a diagram showing time frequency windows for a short-time Fourier transform (STFT)

As seen in FIG. 3, the width of the time-frequency window is unchanged within the spectrum at all frequencies. Once a window has been chosen for the STFT, then the time-frequency resolution given by Eqs. (4) and (8) are fixed over the entire time-frequency plane since the same window is used at all frequencies. If the signal, for example, is composed of small bursts associated with long quasi-stationary components, then each type of component can be analyzed with either good time resolution or good frequency resolution, but not both. This is the Heisenburgh uncertainty principle, and can be described by:

$$\Delta t \cdot \Delta f \geq \frac{1}{4\pi} \quad (13)$$

For abdominal EGG signals, the frequency range of the slow waves is about 2–6 cpm, and the frequency range of the high frequency component of the spike activity is about 4–5 times the frequency of normal slow waves. If high frequency resolution is required in the slow waves analysis for any small shift of the frequency, the width of the time-window should be wide enough to cover several cycles of the slow wave. For example, if a frequency resolution of 1 cpm is desired, the duration of the time window should be about 2 minutes according to Eq. (11). When this window is used to analyze the spike activity in the same EGG signals, the window will cover 2 minutes of the EGG data or about 6 cycles of normal slow waves. It is thus too wide to localize the spike activity even in one period of the slow waves. However, if the window is short enough to localize the higher frequency components in each cycle of the normal slow waves, the width of the time-window should be less than the 0.3 minute (one cycle of the slow waves). The width of the frequency window will then be about 6 cpm which is too wide to analyze the frequency changes of slow wave.

Continuous Wavelet Transform (CWT)

From the discussion above, it should be understood that the window function g(t) of any STFT is rigid, and hence, is not effective for detecting signals with high frequencies superimposed with low frequencies. To overcome this problem, one can let the resolution $\Delta t$ and $\Delta f$ vary in the time-frequency plane in order to obtain a multi-resolution analysis. Intuitively, when the analysis is viewed as a filter bank, the time resolution must increase with the central frequency of the analysis filter. It is therefore required that $\Delta f$ is proportional to f:

$$\frac{\Delta f}{f} = c \quad (14)$$

where c is a constant. The analysis filter bank is then a bandpass filter with constant relative bandwidth (so-called 'constant-Q' analysis). When this kind of filter bank is used, the frequency resolution $\Delta f$ and time resolution $\Delta t$ change with the center frequency of the analysis filter. They must still obey the uncertainty principle, but now, the new 'window' is time-width adapted to its frequency, and is narrow at high frequency and broader at low frequency. As a result, the time resolution becomes arbitrarily good at high frequency, and the frequency resolution becomes arbitrarily good at low frequency. This kind of analysis works best if the signal is composed of high frequency components of short duration plus low frequency components of long duration, which is the case with abdominal EGG signals.

The Continuous Wavelet Transform (CWT) follows exactly these ideas with an additional simplification: all impulse responses of the filter bank are defined as scaled (i.e. stretched or compressed) versions of the same prototype h(t). That is,:

$$h_a(t) = \frac{1}{\sqrt{a}} h\left(\frac{t}{a}\right) \quad (15)$$

where a is a scaled factor and the constant $1/\sqrt{a}$ is used for energy normalization. This results in the definition of the CWT:

$$X^{CWT}(b, a) = \frac{1}{\sqrt{a}} \int x(t) h^*_{a,b} \frac{(t-b)}{a} dt \quad (16)$$

We can see from Eq. (16) that, as a changes, the $_{a,0}$=a$^{-\frac{1}{2}}$h(t/a) covers different frequency ranges. Large values of the scaling parameter a correspond to small frequencies, or large scale $h_a$; small values of a correspond to high frequencies or very fine scale $h_{a,0}$. Changing the parameter b as well allows the movement of the time localization center, i.e., each $h_{a,b}(t)$ is localized around t=b.

Since the same prototype h(t), called the basic wavelet, is used for all of the filter impulse responses, no specific scale is privileged, i.e., the wavelet analysis is self-similar at all scales. Moreover, this simplification is useful when deriving mathematical properties of the CWT.

Preferably, the Gaussian function in Eq. (7) is used as the basic wavelet h(t):

$$h(t) = \frac{1}{2\sqrt{\pi\alpha}} e^{\frac{t^2}{4\alpha}} e^{j2\pi f_0 t} \quad (17)$$

although one skilled in the art will recognize that other appropriate functions may be used as the basic wavelet h(t) without departing from the spirit and scope of the present invention. Assuming the Gaussian function is used, the width of the time window of $h_{a,b}(t)$ is:

$$\Delta t^2 = \frac{\int t^2 |h_{a,b}\frac{t-b}{a}|^2 dt}{\int |h_{a,b}\frac{t-b}{a}|^2 dt} = a^2\alpha, \Delta t = a\sqrt{\alpha} \quad (18)$$

And the width of the frequency window is:

$$\Delta f^2 = \frac{\int f^2 |H_{a,b}(f)|^2 df}{\int |H_{a,b}(f)|^2 df} = \frac{1}{(4\pi)^2 a^2 \alpha}, \Delta f = \frac{1}{2\pi a \sqrt{\alpha}} \quad (19)$$

where $H_{a,b}(f)$ is the Fourier transform of $h_{a,b}(t)$, or:

$$H_{a,b}(f) = \frac{1}{\sqrt{a}} \int_{-\infty}^{\infty} e^{-j2\pi ft} h_{a,b} \frac{t-b}{a} dt \quad (20)$$

$$= \sqrt{a} \cdot H_{a,b}(af) e^{j2\pi bf} \quad (21)$$

Eq. (16) can therefore be rewritten after substituting x(t) as the inverse Fourier transform of X(f), and by replacing $H_{ab}(f)$ with $H_{ab}(af)$ from Eq. 21, we have:

$$X^{CWT}(b, a) = \sqrt{a} \int H^*(af)X(f)|e^{j2\pi fb}df \quad (22)$$

This implies that the CWT at scale a and shift b can be computed by taking the inverse Fourier transform of $H^*(af)$ $X(f)$ where the shift parameter b becomes the time instead of t. The product of the time and frequency width is the same as Eq. (11). The rectangular time-frequency window is now:

$$|b - a\sqrt{\alpha}, b + a\sqrt{\alpha}| \times \left[ f - \frac{1}{4\pi a \sqrt{\alpha}}, f + \frac{1}{4\pi a \sqrt{\alpha}} \right] \quad (23)$$

in the t-f plane. The scaling parameter a adjusts the width of time and frequency windows, and the relation with the Q value is expressed as:

$$Q = \frac{f}{2\Delta f} = 2\pi \sqrt{\alpha} \ af_o \quad (24)$$

Figure 4:
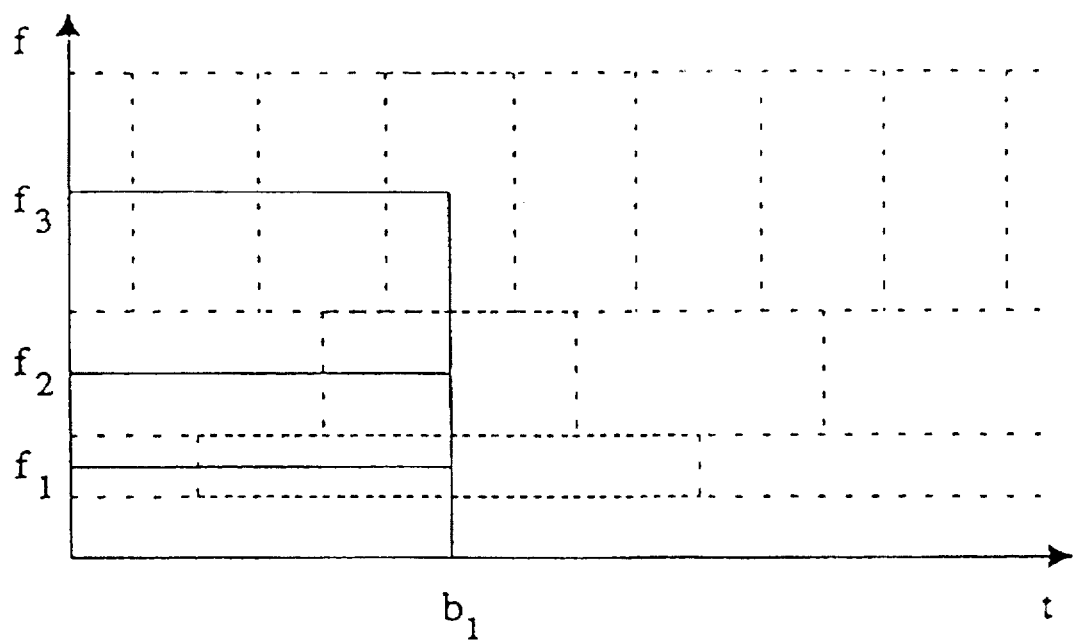
FIG. 4 is a diagram showing time-frequency windows for the Continuous Wavelet transform (CWT) of the present invention.
Figure 5:
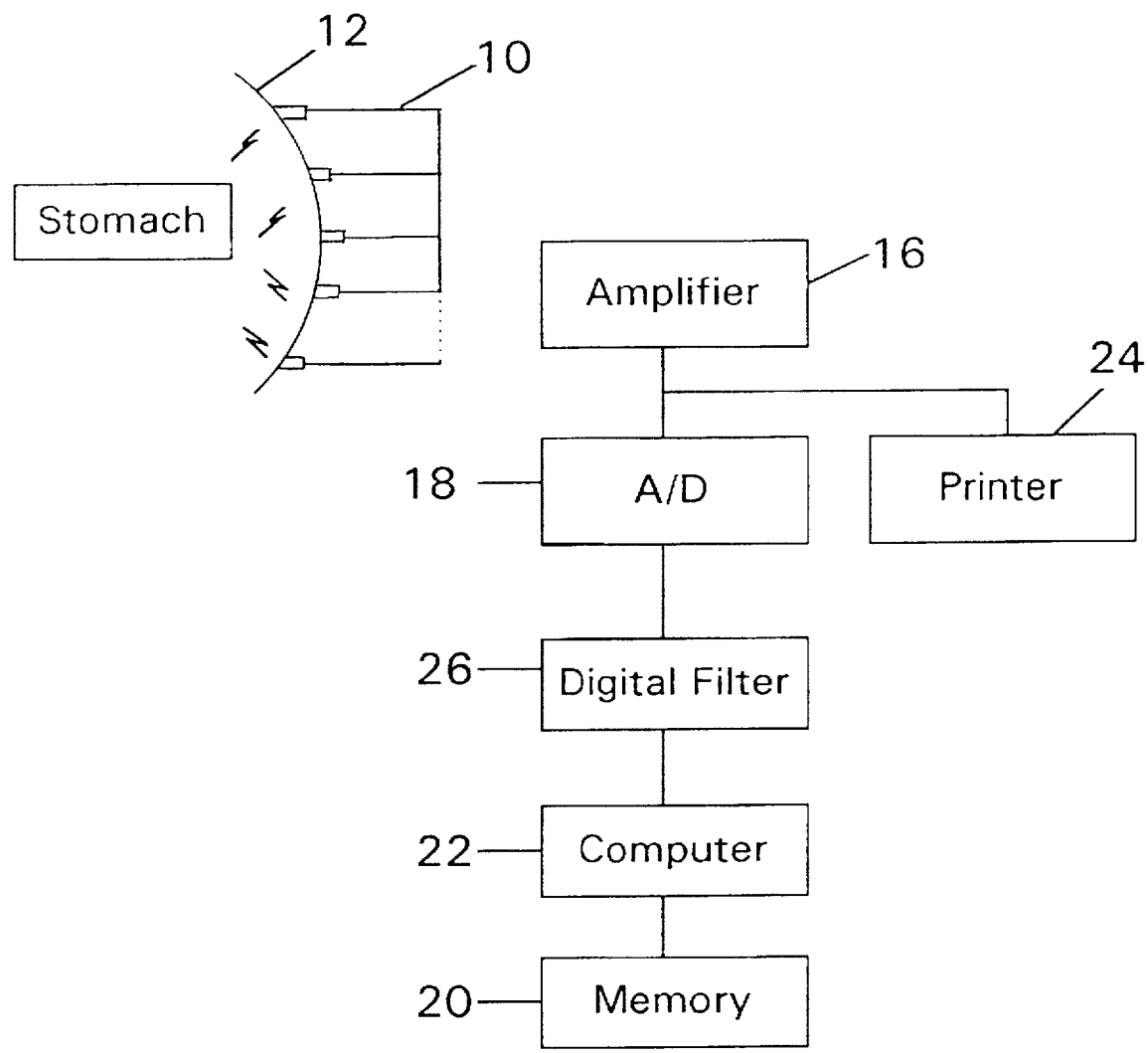
FIG. 5 is a block diagram showing a preferred embodiment for implementing the method of the present invention.

For a constant-Q filter bank, the time window automatically narrows for detecting high frequency phenomena (i.e., small a>0), and widens for investigating low frequency behavior (i.e., large a>0), as shown in FIG. 4.

Implementation

In one embodiment of the present invention, and referring now to FIGS. 5 and 15–19, the system and method are implemented as follows. Electrodes 10 are placed on the abdominal skin 12 adjacent a subject's stomach 14 to input EGG data (151 in FIG. 15). The number and placement of the electrodes 10 may of course be varied based on individual considerations without departing from the spirit and scope of the present invention. For example, the electrodes 10 may be placed to obtain multiple channels of electrical signals. The channels of electrical signal are then amplified by an appropriate amplifier 16, converted to digital data by an appropriate analog-to-digital converter (A/D) 18, and then recorded as data in the memory 20 of an appropriately configured computer 22. Additionally, the amplified channels may be forwarded to an appropriately configured printer 24 for paper recordation.

Preferably, the A/D converter 18 is a multiple channel, 12 bits precision A/D converter with channel select and controllable sampling rate. The A/D converter 18 may also have a display screen and storage memory (not shown). Preferably, to avoid any loss of useful information about the gastric electrical activities, the sampling rate is set at 50 Hz, which is high enough to collect electrocardiac (EKG) signals simultaneously. Preferably, the printer 24 is a chart recorder. Preferably, spike activity if desired is induced by injections of dopamine or epinephrine into the subject.

As was discussed above, the normal frequency of the gastric slow waves is 2–6 cpm, and the high frequency component from gastric spike activity is about 10–12 cpm. The 'raw' collected EGG data contains EKG signals whose frequency is about 60–70 cpm and therefore must be pre-processed (152 in FIG. 15). A digital filter 26 is therefore employed to eliminate the interference from EKG signal. The digital filter 26 may have finite-duration impulse response (i.e., a FIR filter) and therefore would have the advantages of linear phase and stability. However, if the digital filter 26 has infinite-duration impulse response (i.e., an IIR filter), better performance with lower filter order is provided. Nonlinear phase distortion associated with an IIR filter can be overcome by applying the filter 26 to the data in both forward and reverse directions. Preferably, the digital filter 26 is an IIR filter with an order of 12, and a cut-off frequency adjustable between 30–150 cpm (0.5–2.5 Hz). Preferably, the filtered data is down-sampled (162 in FIG. 16) by a factor of from 10 to 50 (i.e., from 50 Hz to 1–5 Hz) which is equivalent to 60–300 cpm and still high enough to avoid the loss of any information in the EGG signals. The down-sampled data is then filtered to remove any net DC component (163 in FIG. 16).

Figure 15:
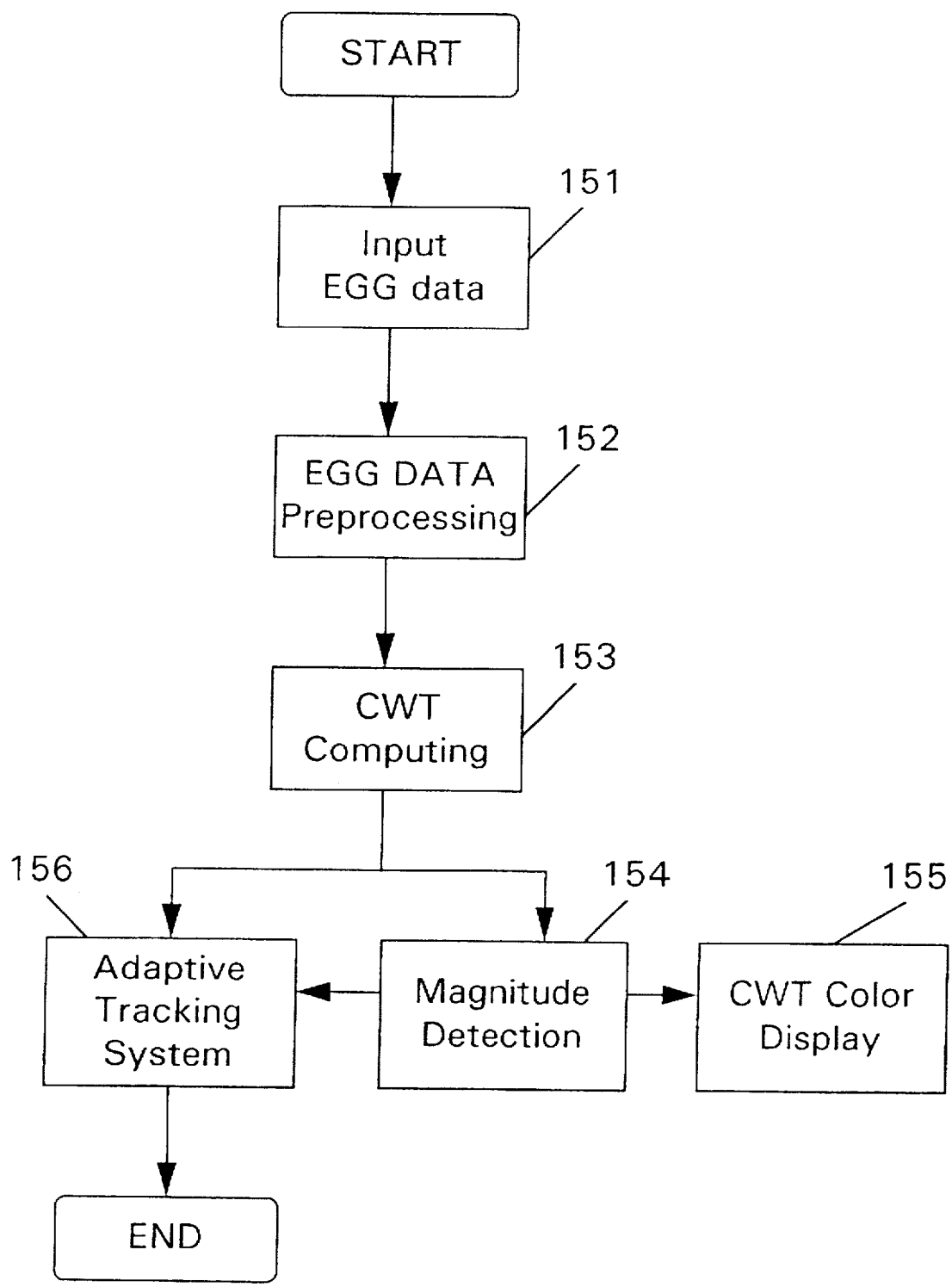
FIGS. 15–19 are flow chart diagrams showing a preferred embodiment for the processing of the EGG signal in the present invention.
Figure 16:
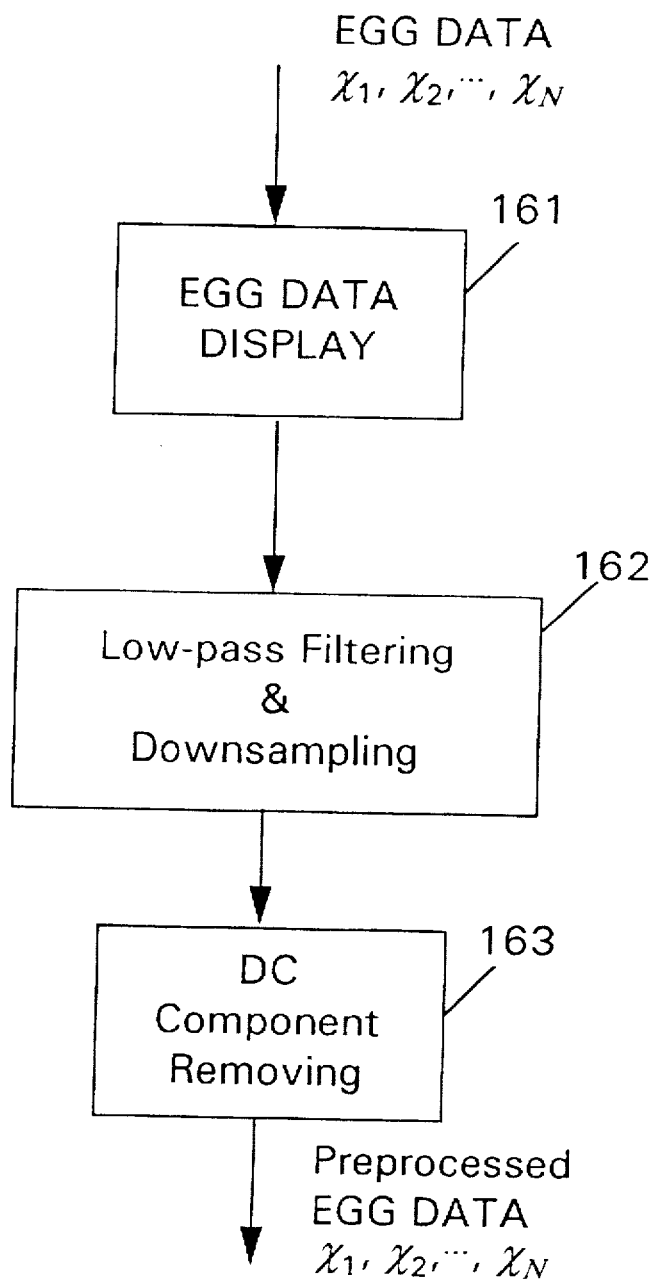
Figure 17:
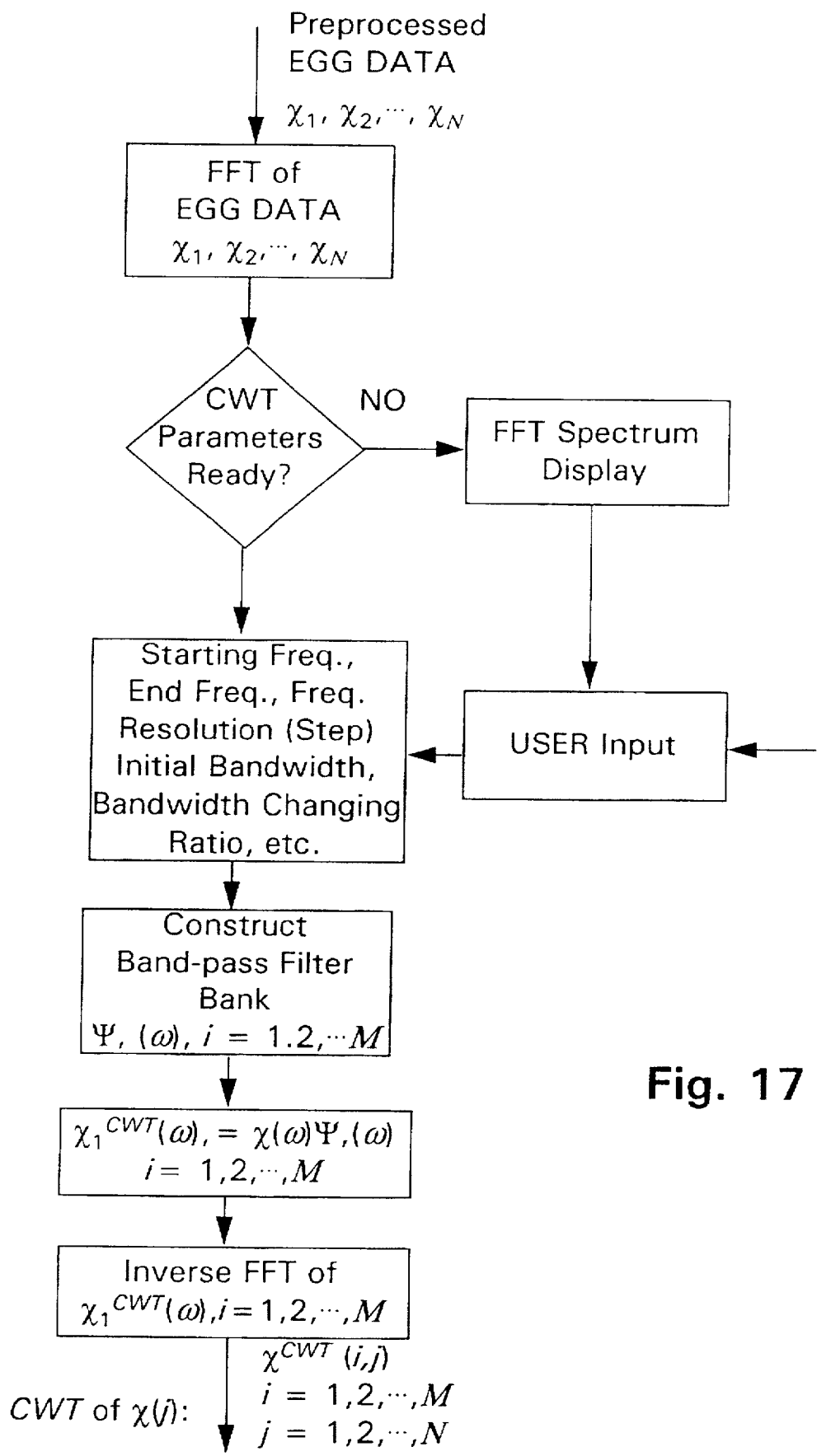
Figure 18:
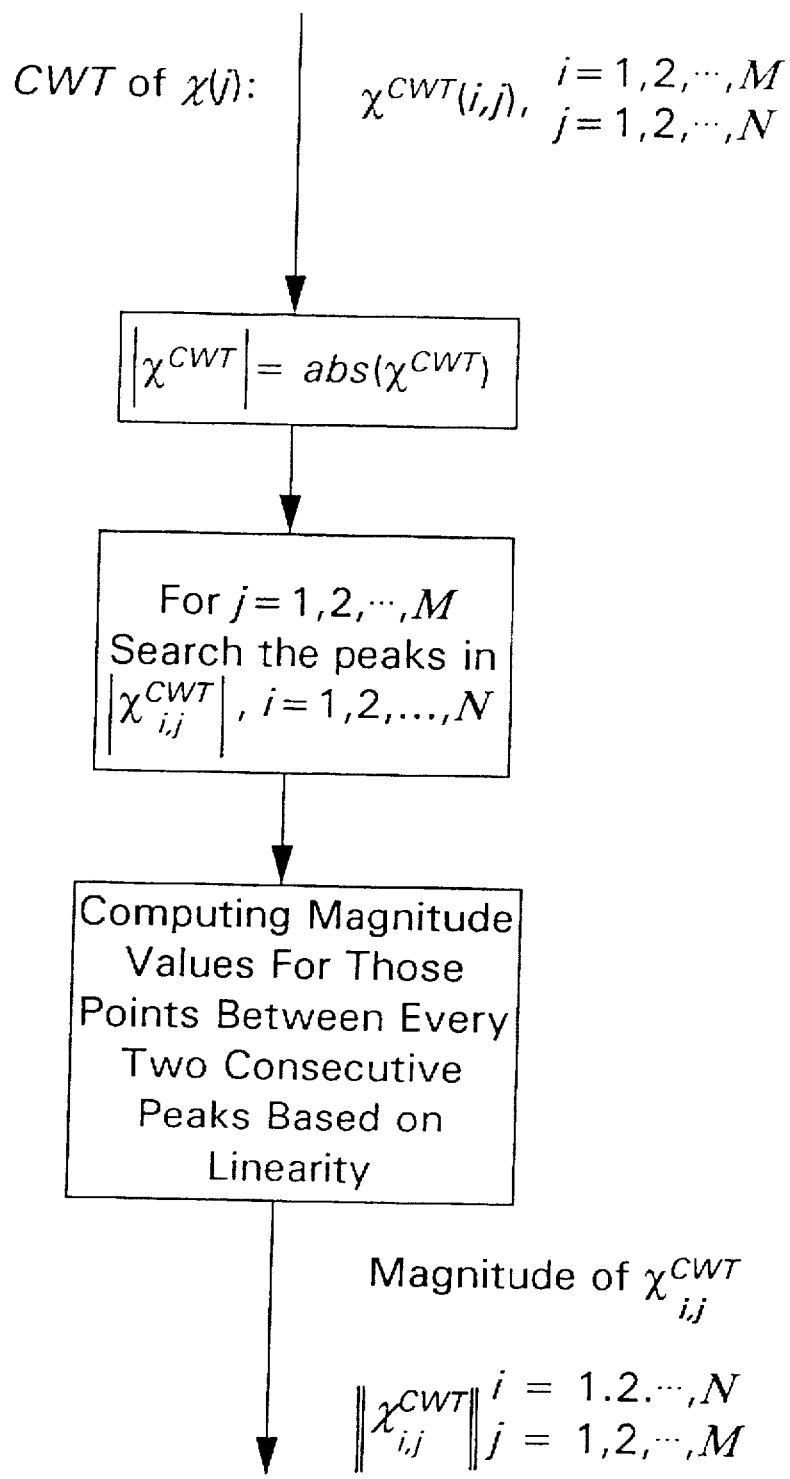
Figure 19:
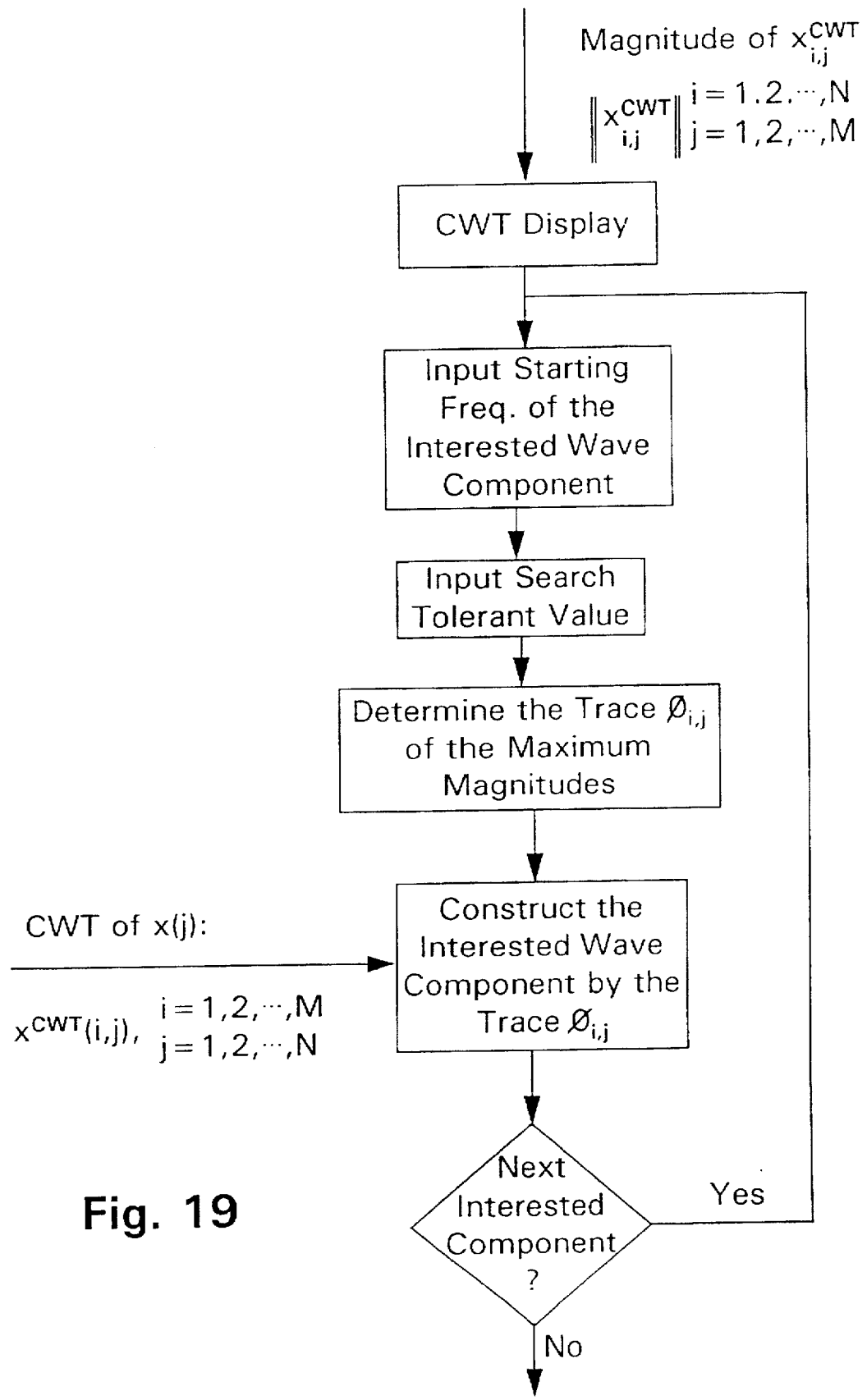

With the data thus gathered, CWT analysis may be performed (153 in FIG. 15; FIG. 17). In the analysis, the parameter $\propto$ of the Gaussian function is set for Eq. (17) and Eq. (20) to be 0.69315, and the parameter a is set to be 2, although one skilled in the art will recognize that the optimal value for the parameter a will vary for each EEG signal, and the value of the parameter a is based on the desired Q value, as expressed in (Eq. 24). The time and frequency Gaussian window functions, respectively, for CWT are:

$$h(t) = \frac{1}{2\sqrt{\pi\alpha}} e^{\frac{t^2}{4\alpha}} \quad (25)$$

$$H_{a,b}(f) = \frac{1}{\sqrt{a}} \int_{-\infty}^{\infty} e^{-j2\pi ft} h_{a,b} \frac{t-b}{a} \, dt \quad (26)$$

The scaling parameter a for CWT is determined by the center frequency and the Q value. Preferably, the Q value is set to be constant for the wavelet analysis. When the center frequency moves or changes, the value of a can be calculated by Eq. (24). The initial Q value is set by analyzing the slow waves with normal frequency, i.e., 3–5 cpm, the width of the frequency window is 1 cpm, and the Q value is unchanged. When the center frequency moves higher, for example, to 4 cpm from 3 cpm, a new value of the parameter α can be easily obtained by Eq. (24). Therefore, a new time or frequency window is obtained to do CWT analysis at the next center frequency.

Figure 6:
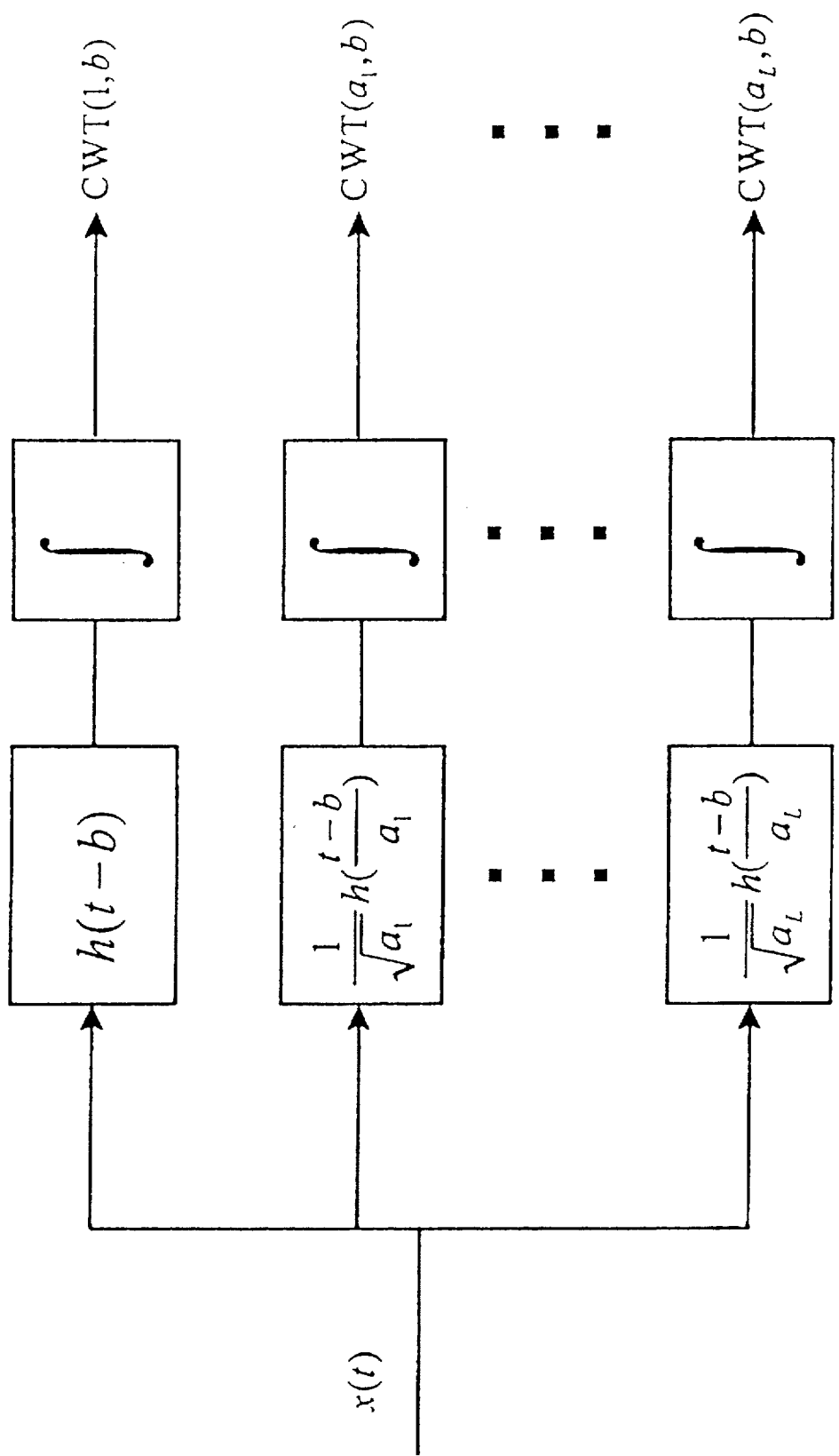
FIGS. 6 and 7 are diagrams showing a filter bank implementation of the CWT in the time domain and in the frequency domain, respectively.
Figure 7:
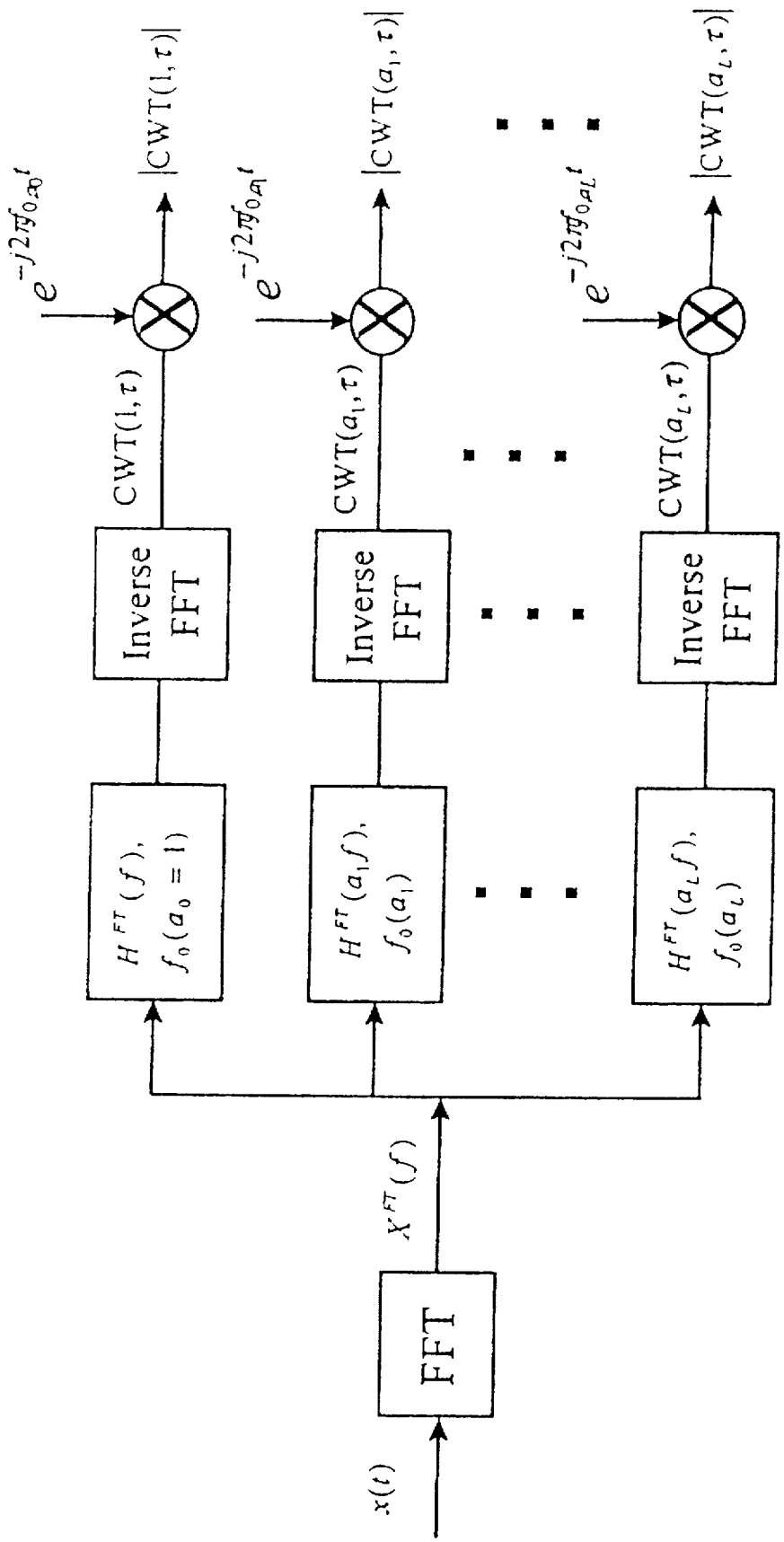

During the computer analysis, only one window is set, either time window or frequency window, depending on whether the analysis is performed on time domain or frequency domain. In time domain, the algorithm of the CWT is the inner moving production or convolution of the EGG data sequence with the time window. The advantage of the analysis on time domain is that it can be performed in real-time mode. In addition, the implementation of CWT in the frequency domain using the fast Fourier transform (FFT) algorithm decreases the number of arithmetic multiplication and additions very efficiently. This is done by truncating the EGG data sequence into several small blocks with the same length for each block. The FFT of Eq. (20) is then employed to obtain the spectrum of each block of data, as shown in FIG. 6. The block data is then transformed into the time domain again using the inverse FFT of Eq. (22), and combined into a long sequence having the original signal length. Accordingly, the output of the CWT is actually the output of the frequency filter bank schematically shown in FIG. 6. As a result, the carrier frequency ($f_o$) of each output channel in FIG. 6 must be removed. As shown in FIG. 7, this is achieved by multiplying each output channel with the negative of the respective carrier frequency so that only the magnitude information of the output channel remains. Since the FFT corresponds to the circular convolution of two data sequences (EGG block data and window), the technique of zero padding or overlapping-add must be used to ensure that the circular convolution has the effect of linear convolution.

Figure 8:
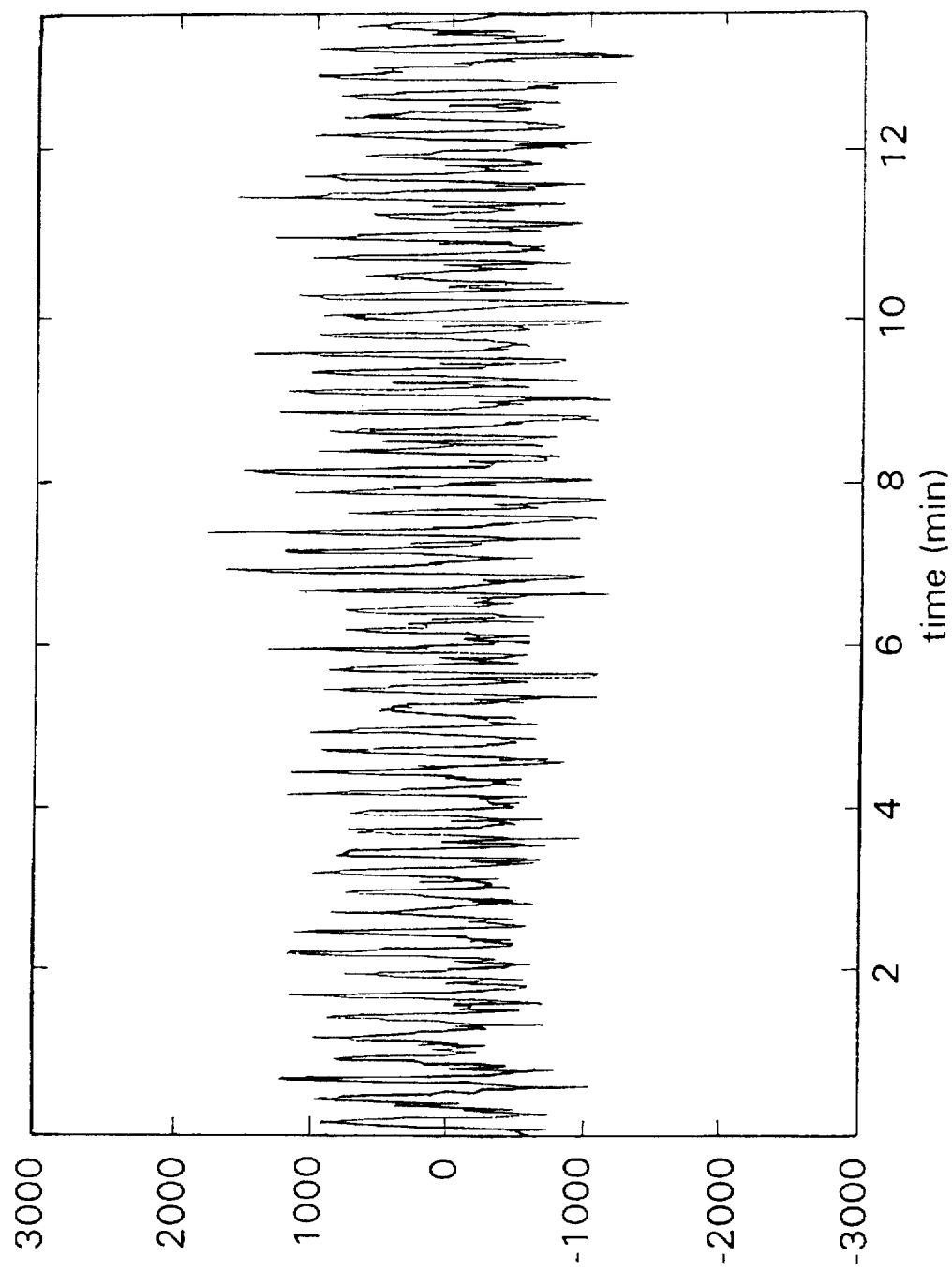
FIGS. 8 and 9 are diagrams showing abdominal EGG signals in the time domain without and with spike activity, respectively.
Figure 9:
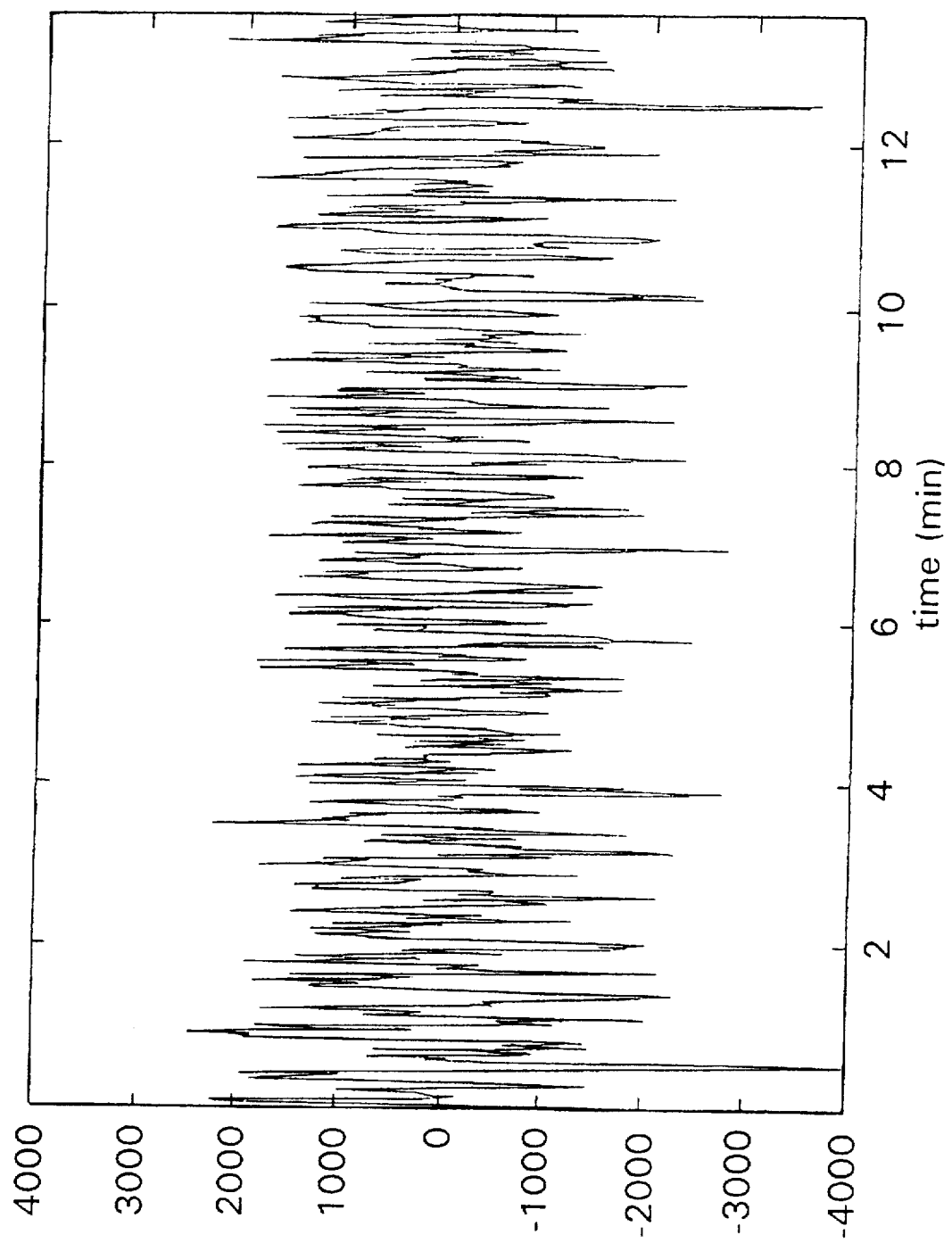
Figure 10:
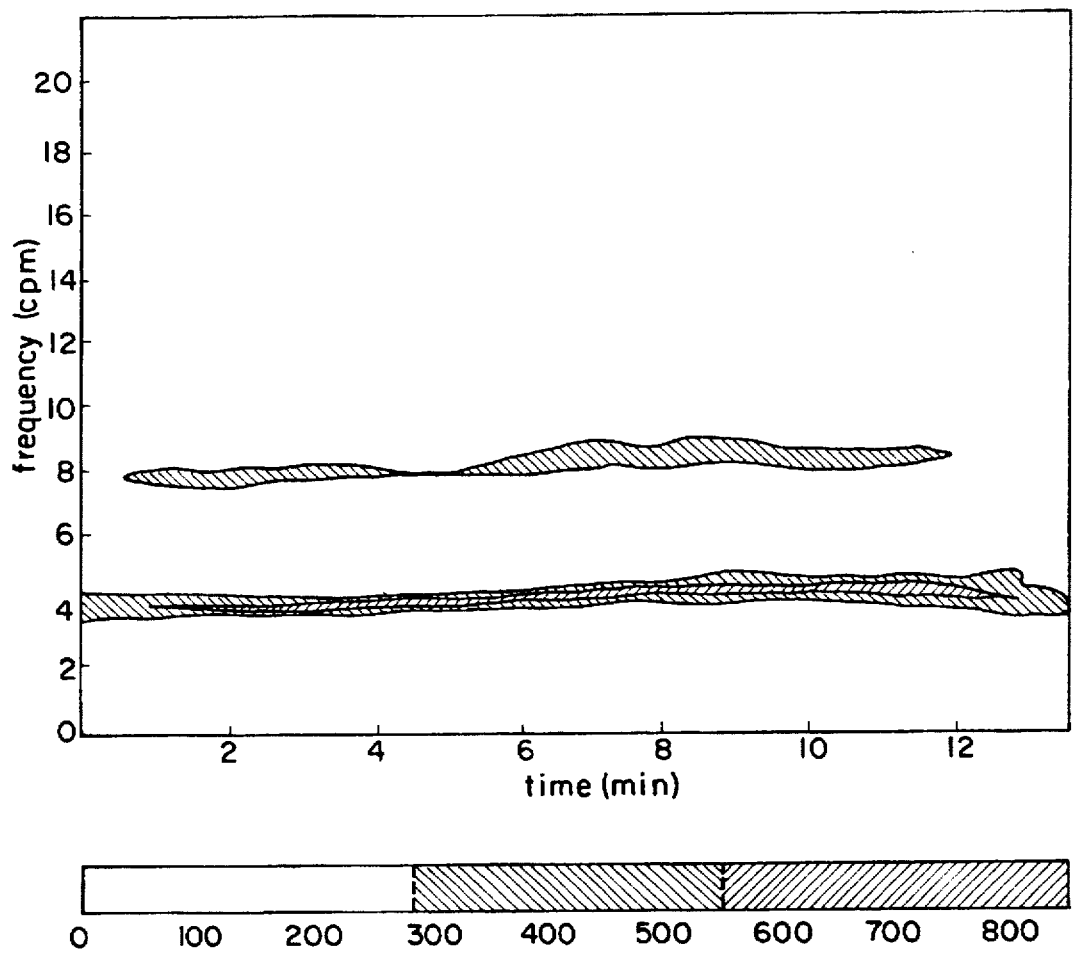
FIGS. 10 and 11 are diagrams showing the respective abdominal EGG signals of FIGS. 8 and 9 in the CWT frequency domain.
Figure 11:
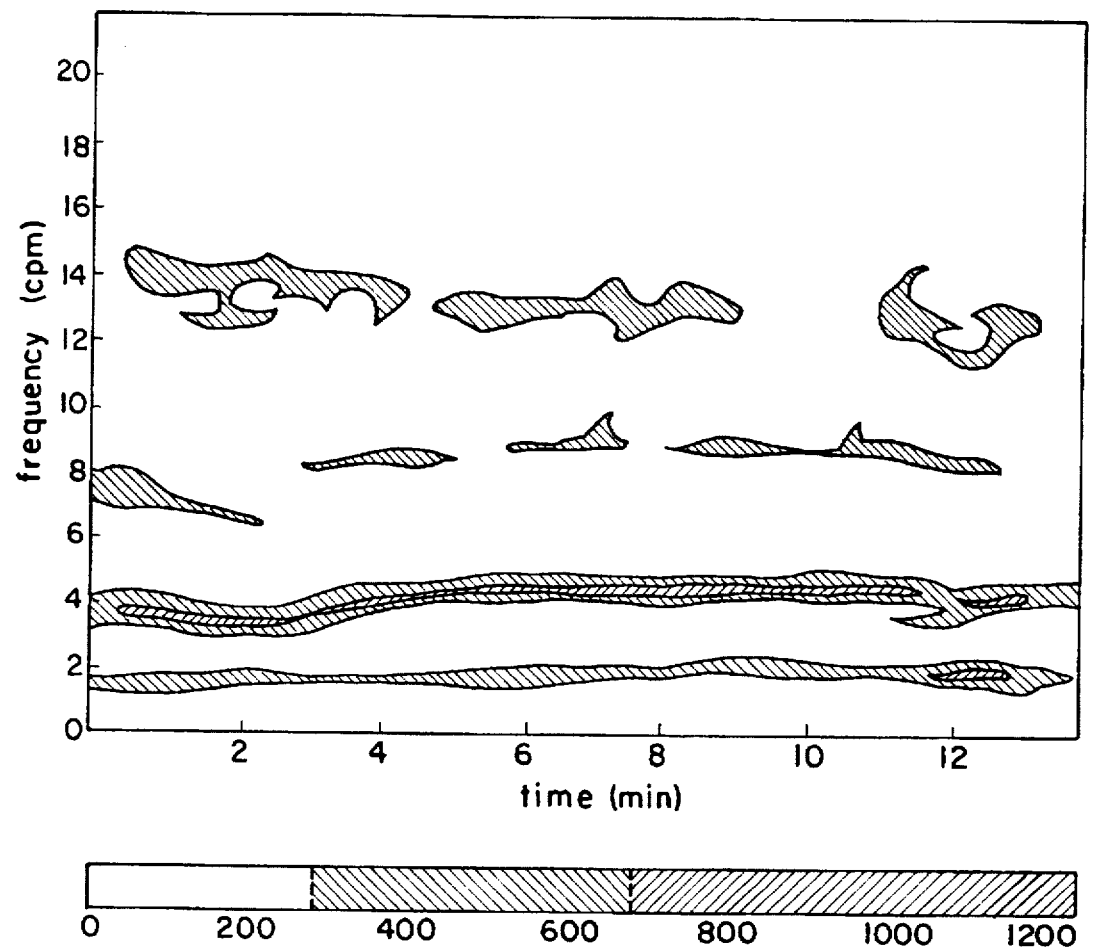

FIGS. 8–11 are the results of a time-frequency multi-resolution analysis of abdominal EGG signals. FIGS. 8 and 9 are abdominal EGG signals in the time domain (i.e., amplitude vs. time). FIGS. 10 and 11 are the respective abdominal EGG signals of FIGS. 8 and 9 in the CWT frequency domain (i.e., frequency vs. time).

FIGS. 8 and 10 are the analysis results of the EGG signal taken before spike activity is induced. FIGS. 9 and 11 are the analysis results of the EGG signal taken after spike activity is induced. Each EGG signal segment is 12 minutes long. The figures show the frequency scales of slow waves, spike waves, and the lower and higher components of slow waves. The highest magnitude lines of frequency occur at about 3.9 to 4.1 cpm and represent slow waves of the EGG signals. The arrhythmia of the stomach, such as tachygastria and bradygastria are not observed in FIGS. 8 and 10 since the frequencies of the slow waves fall into normal ranges and have little change. The lines at about 8 cpm in FIG. 10 are believed to be harmonics of the slow waves.

As seen in FIG. 11, below the frequency of the slow waves, there appears a strong lower frequency line representing spike activity. The frequency scale of the lower frequency line is about half the slow wave or about 1.9 to 2 cpm. There are also higher frequency lines in FIG. 11 in the frequency range of about 8 to 14 cpm. These lower and higher frequency lines are obviously lacking in the non-spike EGG graph of FIG. 10. As seen, the lower frequency line is as stable as that of the slow waves while the higher frequency line changes with time.

The spike graph of FIG. 11 clearly shows that CWT analysis can be employed with an EGG signal to display several demarcated frequency components including the slow wave, the half-frequency of the slow wave, and the high frequency component representative of spike activity. Moreover, since the CWT analysis can be performed while the EGG signal is being sampled, the analysis may essentially be done in real time.

Figure 12:
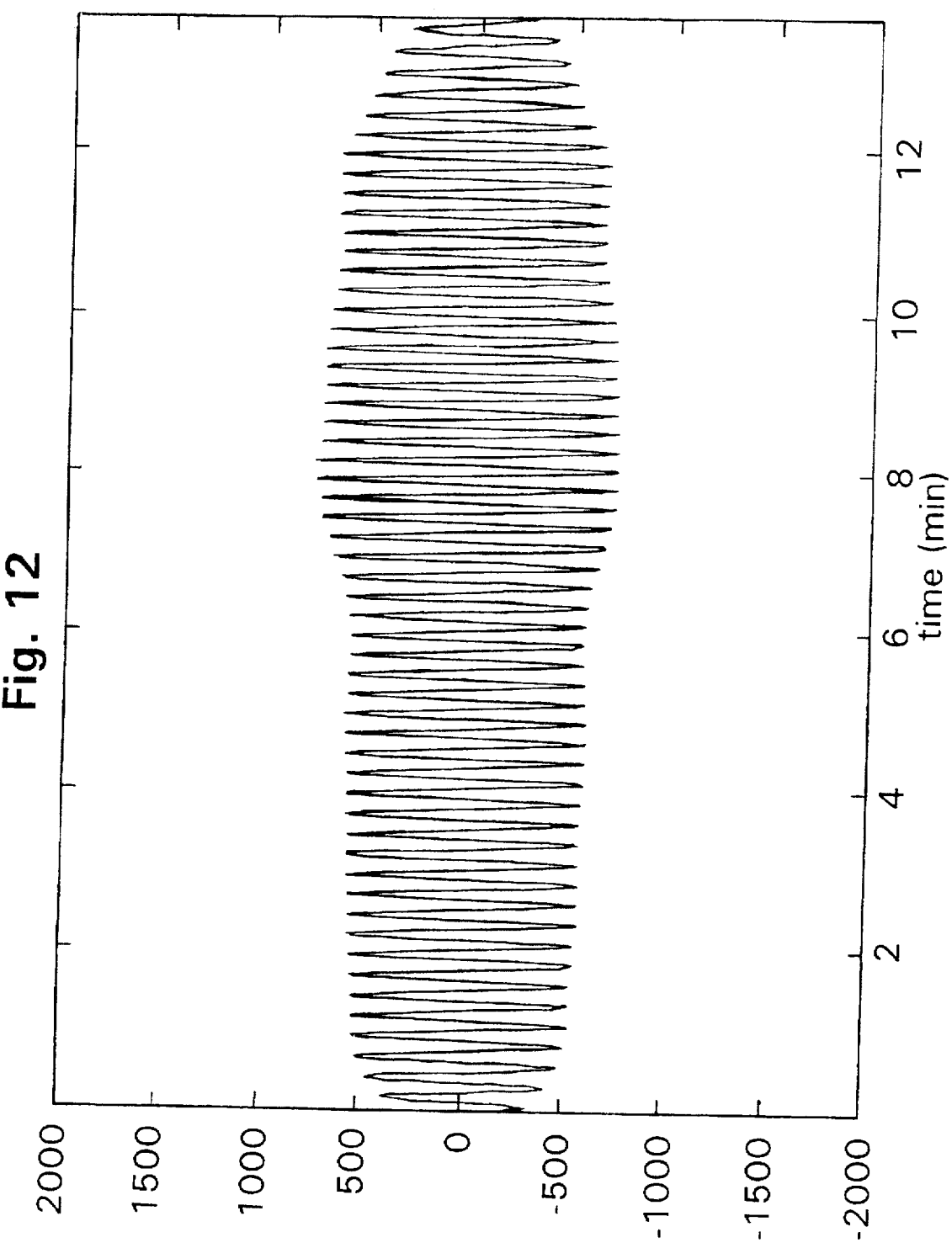
FIG. 12 is a diagram showing the slow wave extracted from the CWT abdominal EGG signal of FIG. 8.
Figure 13:
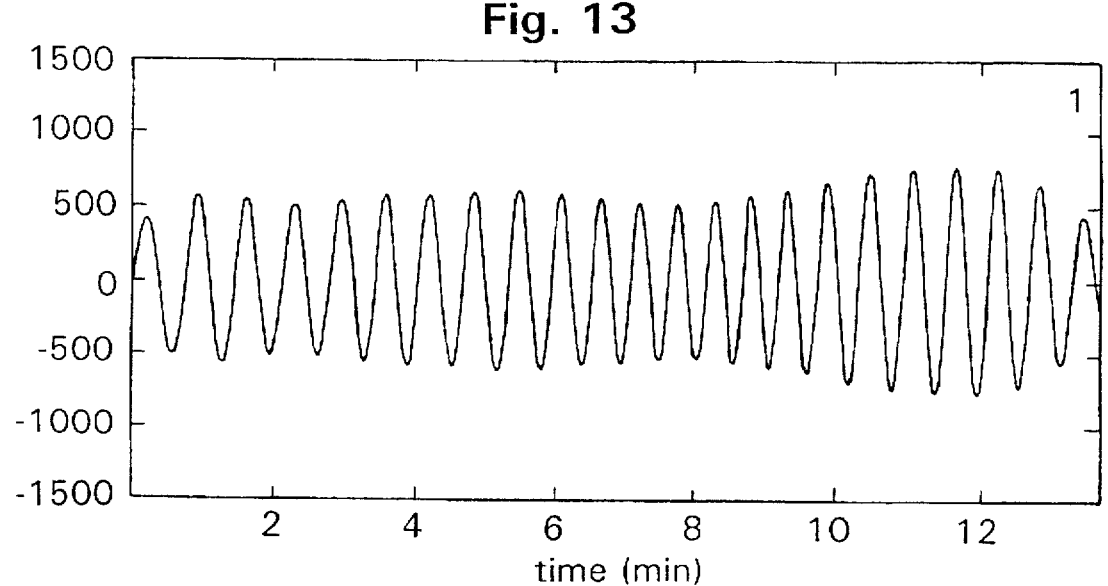
FIGS. 13 and 14 are diagrams respectively showing the slow wave and spike activity extracted from the CWT abdominal EGG signal of FIG. 9.
Figure 14:
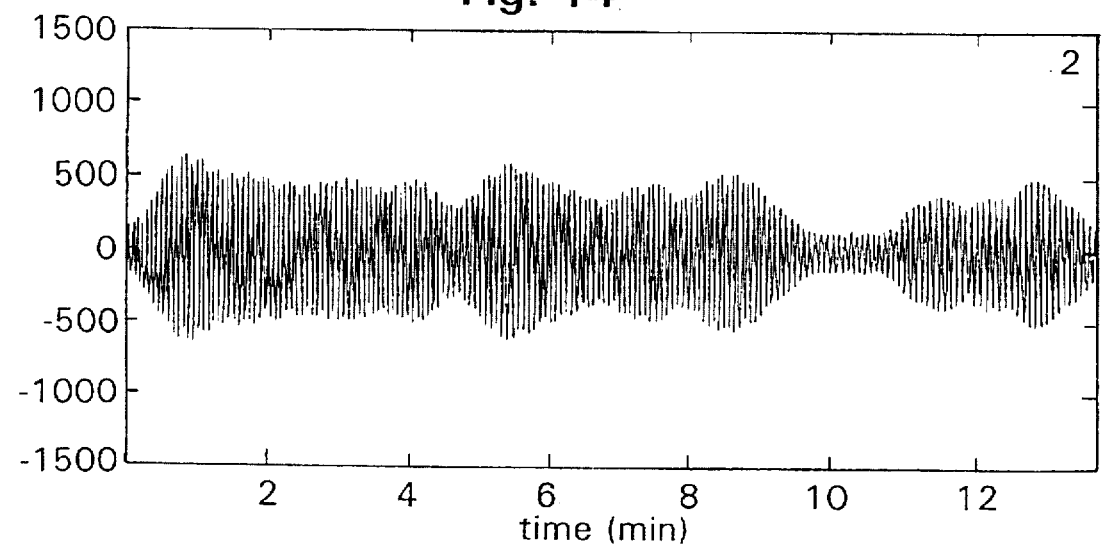

Preferably, an Adaptive Tracking System (ATS) (156 in FIG. 15) is used to extract the slow wave (FIGS. 12 and 13, which respectively correspond to the non-spike and spike graphs of FIGS. 10 and 11), and the spike activity (i.e., the high frequency component) (FIG. 14, which corresponds to the spike graph of FIG. 11) from the results of the CWT analysis. The ATS employs a narrow band-pass filter with adaptive center frequency representative of spike activity. Preferably, the ATS operates on the principle of frequency magnitude searching at each time interval. At each point of time, maximum magnitude detection (154 in FIG. 15) is employed to search for the next available point, as should be understood from FIG. 18. From the detected magnitudes, a display (155 in FIG. 15) may be employed to visually render the result of the CWT analysis. The ATS frequency information is obtained by following the movement from point to point in adaptation to the detected magnitudes of the desired frequency, as should be understood from FIG. 19.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

We claim:

1. A method of analyzing an electrogastrophic (EGG) signal, comprising the steps of:

placing electrodes on abdominal skin of a subject adjacent a stomach thereof, the stomach producing the EGG signal;

obtaining the produced EGG signal by way of the electrodes;

amplifying the obtained EGG signal by way of an amplifier; and transforming the amplified EGG signal from a time domain representation to a frequency domain representation by way of a predetermined transform function incorporating a variable frequency and a window function having a time resolution and a frequency resolution, the frequency resolution of the window function being proportional to the frequency, the time resolution of the window function varying with the frequency such that the time resolution is relatively narrow when the frequency is relatively high and relatively broad when the frequency is relatively low.

2. The method of claim 1 further comprising the steps of storing the amplified EGG signal in a memory and retrieving the stored EGG signal from the memory, wherein the transforming step comprises transforming the retrieved EGG signal.

3. The method of claim 1 further comprising the steps of:

sampling the amplified EGG signals at a predetermined sampling rate; and converting the amplified EGG signals from an analog form to a digital form.

4. The method of claim 3 wherein the subject also produces electrocardiac (EKG) signals, the method further comprising the step of eliminating interference from the EKG signal by way of a digital filter.

5. The method of claim 1 wherein the transforming step comprises transforming the retrieved EGG signal (x(t)) according to a transform function as follows:

$$X^{CWT}(b, a) = \frac{1}{\sqrt{a}} \int x(t) h_{a,b}^* \frac{(t-b)}{a} dt$$

where a is a scaling parameter and b is a time localization parameter.

6. The method of claim 5 wherein the transform function incorporates a basic wavelet function as follows:

$$h(t) = \frac{1}{2\sqrt{\pi\alpha}} e^{\frac{t^2}{4\alpha}} e^{j2\pi f_o t}$$

wherein $\alpha$ is a standard deviation and $f_o$ is a center frequency.

7. The method of claim 1 further comprising the steps of extracting from the transformed EGG signal a predetermined characteristic waveform component of the EGG signal, wherein the component is selected from a group consisting of a slow wave component and a high frequency component.

8. A system for analyzing an electrogastrophic (EGG) signal, comprising:

electrodes adapted to be positioned on abdominal skin of a subject adjacent a stomach thereof, the stomach producing the EGG signal, the electrodes for obtaining the produced EGG signal;

an amplifier connected to the electrodes for receiving the obtained EGG signals, the amplifier for amplifying the obtained EGG signal; and a transforming device operatively connected to the amplifier for receiving the amplified EGG signal, the transforming device for transforming the amplified EGG signal from a time domain representation to a frequency domain representation by way of a predetermined transform function incorporating a variable frequency and a window function having a time resolution and a frequency resolution, the frequency resolution of the window function being proportional to the frequency, the time resolution of the window function varying with the frequency such that the time resolution is relatively narrow when the frequency is relatively high and relatively broad when the frequency is relatively low.

9. The system of claim 8 further comprising a memory device for receiving the amplified EGG signal, the memory device for storing the amplified EGG signal and retrieving the amplified EGG signal, the transforming device being connected to the memory device for receiving the retrieved EGG signal.

10. The system of claim 8 further comprising an analog-to-digital converter interposed between the amplifier and the transforming device, the converter being connected to the amplifier for receiving the amplified EGG signal, the converter for sampling the amplified EGG signals at a predetermined sampling rate and converting the amplified EGG signals from an analog form to a digital form, the transforming device being connected to the memory device for receiving the digital form of the EGG signal.

11. The system of claim 10 wherein the subject also produces electrocardiac (EKG) signals, the system further comprising a digital filter interposed between the converter and the transforming device, the filter being connected to the converter for receiving the converted EGG signal, the filter for eliminating interference from the EKG signal, the transforming device being connected to the filter device for receiving the filtered form of the EGG signal.

12. The system of claim 8 wherein the transforming device transforms the retrieved EGG signal (x(t)) according to a transform function as follows:

$$X^{CWT}(b, a) = \frac{1}{\sqrt{a}} \int x(t) h_{a,b} * \frac{(t-b)}{a} \, dt$$

where a is a scaling parameter and b is a time localization parameter.

13. The system of claim 12 wherein the transform function of the transforming device incorporates a basic wavelet function as follows:

$$h(t) = \frac{1}{2\sqrt{\pi\alpha}} e^{\frac{t^2}{4\alpha}} e^{j2\pi f_o t}$$

wherein $\alpha$ is a standard deviation and $f_o$ is a center frequency.

14. The system of claim 8 further comprising an extracting device for extracting from the transformed EGG signal a predetermined characteristic waveform component of the EGG signal, wherein the component is selected from a group consisting of a slow wave component and a high frequency component.

* * * * *